United States Patent [19]

Lightfoot

[11] Patent Number: 5,132,089
[45] Date of Patent: Jul. 21, 1992

[54] HAND-HELD CRYOFIXATION APPARATUS

[76] Inventor: Fred G. Lightfoot, 1881 Patrick Henry Dr., Arlington, Va. 22205

[21] Appl. No.: 648,892

[22] Filed: Jan. 31, 1991

[51] Int. Cl.⁵ .......................... B01L 7/00; B01L 9/00; A61F 7/00; A61B 17/00
[52] U.S. Cl. .................................... 422/99; 422/104; 606/20; 606/21; 606/22; 606/23; 62/293
[58] Field of Search ............... 232 2/104, 99; 62/62, 62/55.5, 63, 64, 51.1, 52.1, 20, 48.3, 48.1, 78; 606/24, 23, 21, 20, 22, 25

[56] References Cited

U.S. PATENT DOCUMENTS

| 3,369,440 | 2/1968 | Armao | 128/303.1 |
| 3,391,690 | 7/1968 | Armao | 128/2 |
| 3,696,813 | 10/1972 | Wallach | 128/303.1 |
| 3,794,039 | 2/1974 | Kollner et al. | 128/303.1 |
| 4,074,717 | 2/1978 | Rzasa | 128/303.1 |
| 4,236,518 | 12/1980 | Floyd | 128/303.1 |
| 4,376,376 | 3/1983 | Gregory | 62/51 |
| 4,377,168 | 3/1983 | Rzasa et al. | 128/303.1 |
| 4,578,963 | 4/1986 | Sitte | 62/514 R |
| 4,745,764 | 5/1988 | Sitte | 62/78 |
| 4,751,828 | 6/1988 | Coulter | 62/514 R |
| 5,044,165 | 9/1991 | Linner et al. | 62/55.5 |

Primary Examiner—James C. Housel
Assistant Examiner—Long V. Le
Attorney, Agent, or Firm—Jerry C. Lyell

[57] ABSTRACT

A hand-held cryofixation apparatus in the form of a pistol handgrip into which is mounted a pneumatic cylinder and piston rod. A removable adapter and tissue mount is attached to the end of said piston rod. The handgrip is further fashioned with a slot or cutout into which is slidably disposed an L-shaped metal rod, the upturned leg of which supports a mirror finish metal block. Upon activation of the pneumatic cylinder the tissue mount is slammed against the mirror finish metal block which has been precooled by immersion into a cryogen such as liquid nitrogen or helium.

7 Claims, 3 Drawing Sheets

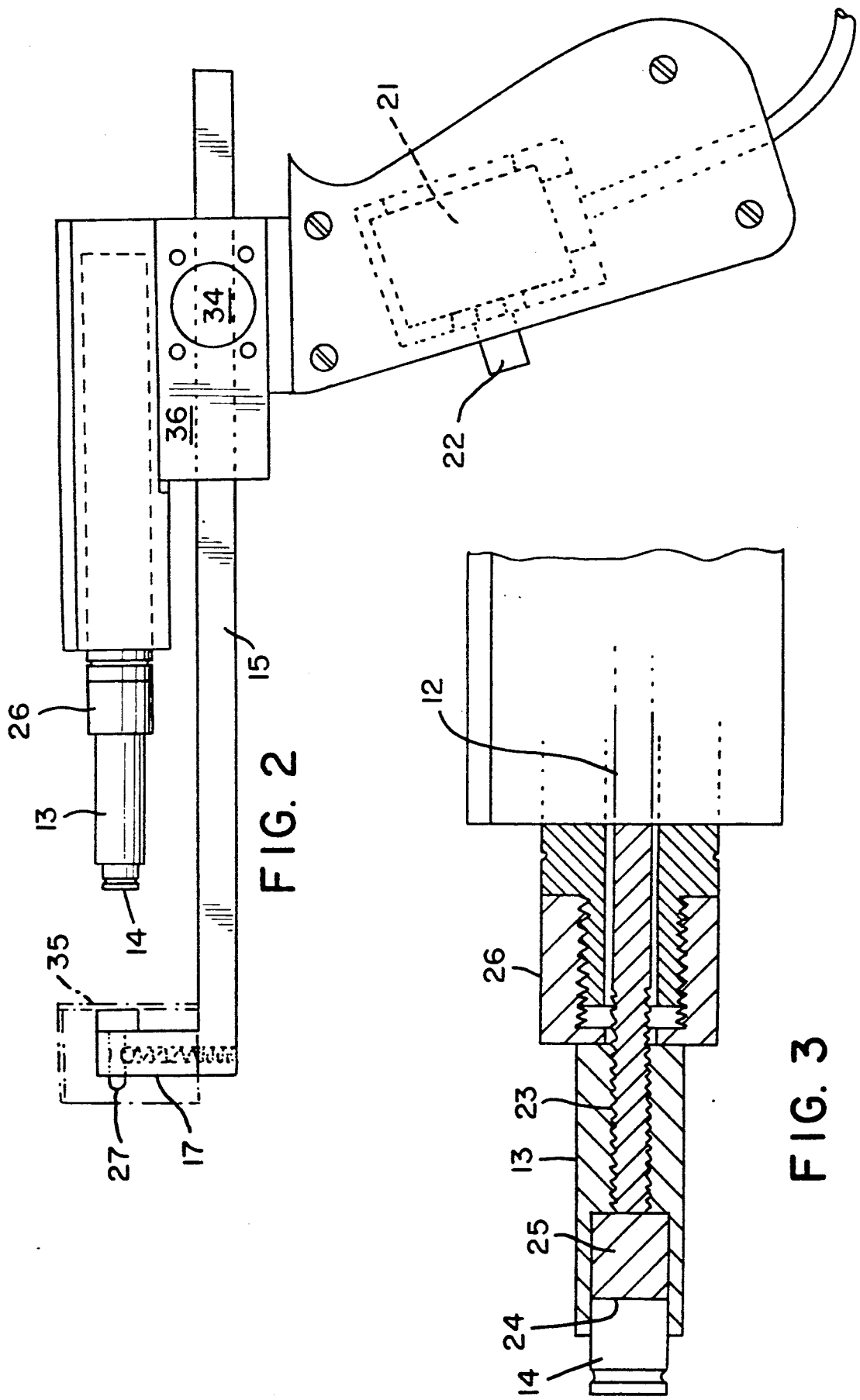

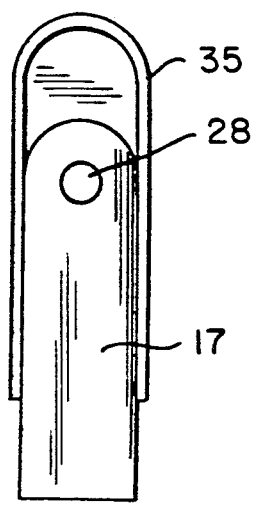
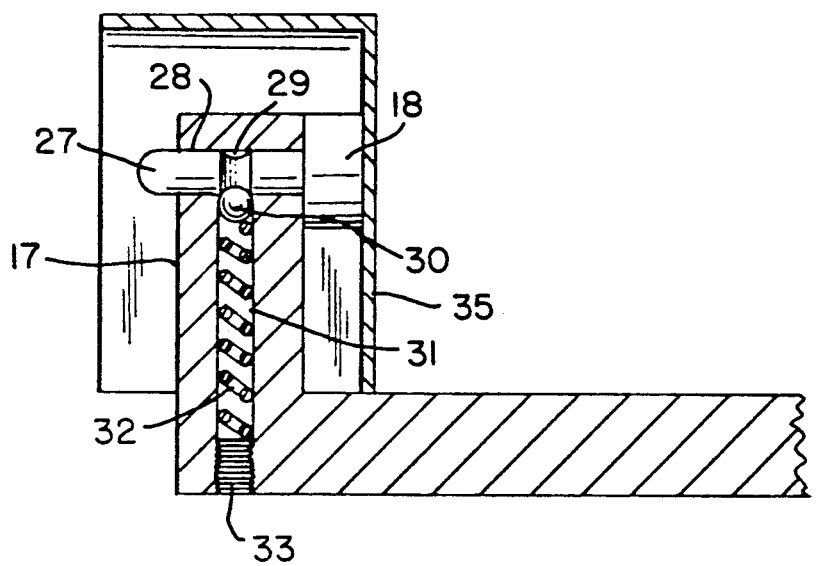
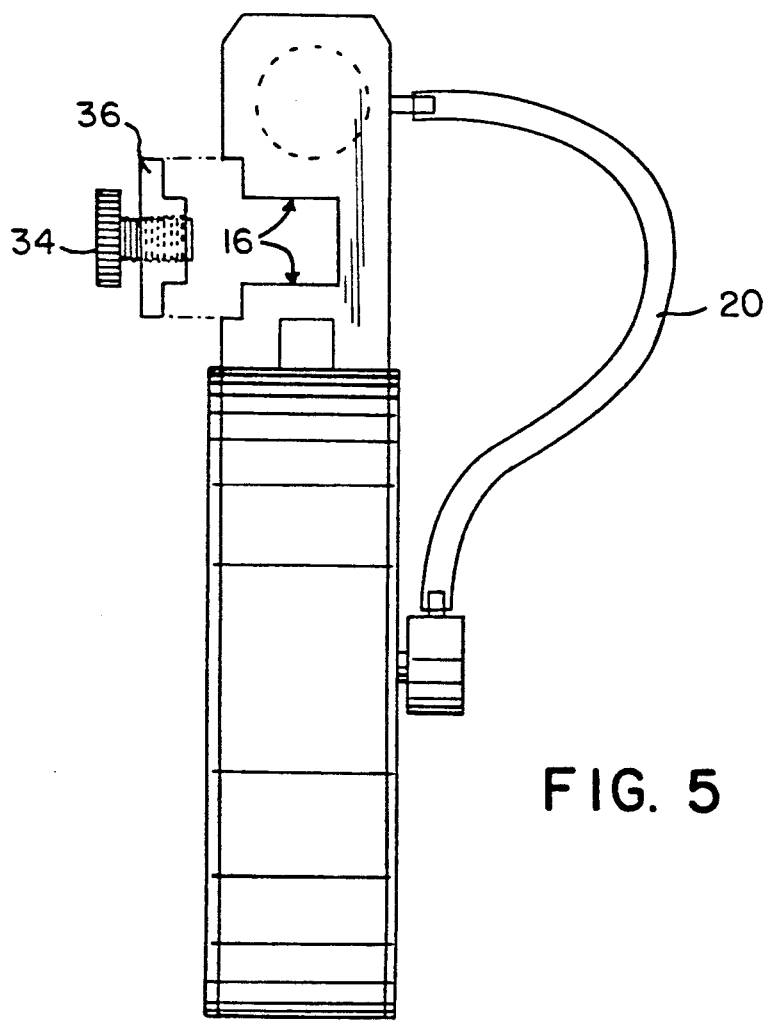

HAND-HELD CRYOFIXATION APPARATUS

BACKGROUND OF THE INVENTION

Microscopic examination of frozen sections of biological specimens has been done for many years but the methods and apparatus for preparing such specimens is in a comparatively early stage of development.

Frozen section specimens are typically prepared either by immersion of the specimen in a cryogen such as liquid nitrogen or helium, or by bringing the specimen into contact with a super cold surface that has been immersed in cryogen. Previously available cryogenic devices have been rather cumbersome assemblages of equipment in the form of fixed or relatively immobile cryogen tanks with bulky specimen immersion contrivances.

The state of the art is revealed in issued patents such as Sitte, U.S. Pat. No. 4,578,963; Sitte et al, U.S. Pat. No. 4,745,764 and Coulter et al, U.S. Pat. No. 4,751,828.

These patents teach various refinements of the cryofixation process but do not teach hand-held capability of such devices in the manner of the present invention.

The Lightfoot device was developed in response to the need to cryofix specimens where they are found, i.e., in vivo or in surgical environments. However, the present invention is not limited to surgery or the like but is able to perform as a general research tool wherever tissue fixations are needed.

SUMMARY OF THE INVENTION

The present invention is a hand-held ultra-rapid tissue freezing device for in situ fixation of biological or polymeric materials.

The device consists of a frame in the form of a pistol handgrip into which is installed a pneumatic cylinder and piston assembly. The end of an outwardly projecting piston rod of the pneumatic cylinder is further fashioned with an adapter and interchangeable tissue mounts.

The frame has a cutout or hole therethrough in which can be mounted an L-shaped metal rod with a metal block with mirror finish on one surface affixed to the upturned leg of the rod and oriented so that the mirrored surface directly faces the line of travel of the pneumatic piston rod and tissue mount.

The invention may be used to cryofix specimens in vitro by mounting tissue specimens on the tissue mount of the retracted pneumatic cylinder and then "firing" the cylinder with a charge of compressed air under a predetermined amount of pressure. Pressure of the compressed air is varied at the option of the user depending upon the thickness or density of the material to be fixed. This procedure, sometimes referred to as "slamming", presses the specimen against the mirrored surface which, prior to activation of the cylinder, has been cooled by immersion in a selected cryogen, i.e., liquid nitrogen or helium. Cryofixation of specimens in vivo may be performed by positioning live tissue between the retracted tissue mount and metal block (in any orientation), and firing the cylinder. Such versatility is especially valuable in pathology where preparation and examination of frozen tissue sections is required incident to surgical procedures.

The fact that the present invention can be operated in any orientation also enables the device to produce improved fixations of cell suspensions and tissue cultures. Currently available devices typically require suspending a drop of cell suspension from an inverted tissue mount which then slams the hanging drop downward against a super cold surface. The first microns of depth of matter to be fixed in this manner are the bottom-most layers of suspension fluid. Fixation proceeds upward through cells or tissue with lessening speed and efficiency resulting in lower cellular integrity of the sample to be studied.

In contrast, the present invention enables the user to hold the device upright such that a drop of cell suspension placed upon the tissue mount can be propelled upward against the pre-cooled metal block with the result that tissue or cells at the surface of the suspension fluid are fixed first upon contact.

The release of air pressure into the pneumatic cylinder is controlled by a trigger-actuated air switch set into the handgrip. There being no significant decay in the air pressure driving the piston rod, rebound of the specimen and tissue mount is prevented, resulting in further improvement of quality of the matter being fixed.

The present invention enables the laboratorian or clinician to easily prepare frozen specimens with minimal crystallization and cellular deformation and to fix specimens in locations that cannot be reached with currently available devices. This invention is readily applicable to cryomicroscopy, elemental x-ray microanalysis, freeze substitution, freeze drying, molecular distillation drying and morphological studies.

BRIEF DESCRIPTION OF THE DRAWINGS

The invention may be further understood by reference to the drawings in which:

FIG. 2 is a side view of the device with the air cylinder piston rod in the retracted position. FIG. 3 is a section taken through the adapter, tissue mount and mount holder. FIG. 4A is a section taken through the metal block, copper rod and brass cover. FIG. 4B is an end view of the upturned leg with brass cover. FIG. 5 is an end view of the frame showing cutout for the metal rod.

DESCRIPTION OF THE PREFERRED EMBODIMENT

Figure 1:
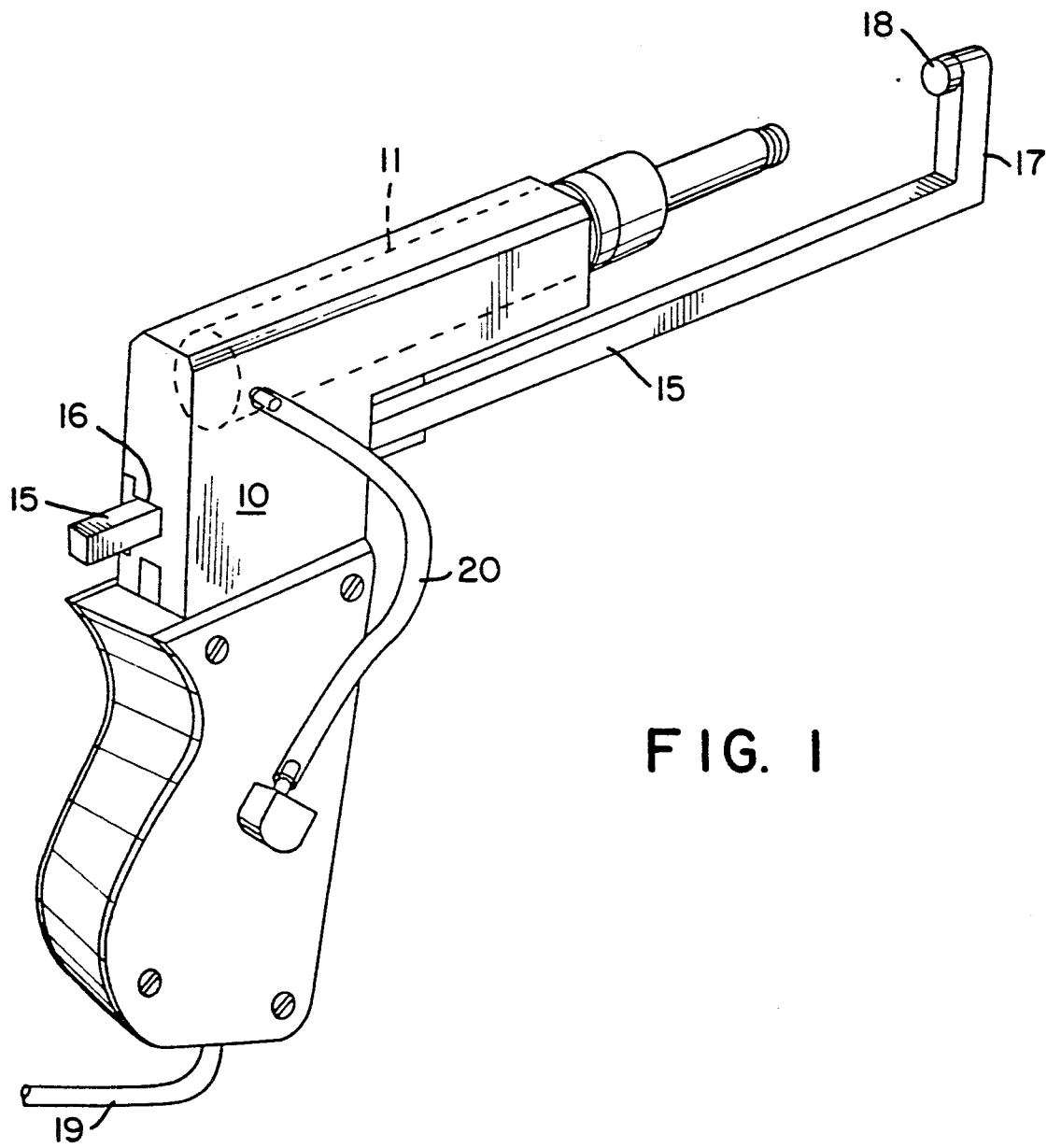
FIG. 1 is an isometric drawing of the device.

Referring now to FIGS. 1, 2 and 3 of the drawings, the present invention comprises a frame in the form of a piston handgrip 10 into which is mounted a pneumatic cylinder 11 and piston rod 12. Said frame can be manufactured of any number of metals, polymers or ceramic materials. The pneumatic cylinder can be selected from among a number of commercially available cylinders. Said piston rod 12 visible in FIG. 3 holds a removable adapter 13 and tissue mount 14.

Shown in FIG. 1 is an L-shaped metal rod 15 which is slidably mounted in a slot or cutout 16 in said frame 10. Said metal rod is preferably manufactured of the purest grade copper. Attached on the upturned leg 7 of said copper rod is a metal block 18 with mirror finish on one surface.

Visible on one side of said frame in FIG. 1 are compressed air inlet tube 19 and pneumatic cylinder charge air tube 20. Said inlet tube 19 conveys compressed air from a tank or pressure regulator to an air switch that is enclosed in said frame and is not visible in this view. Said pneumatic cylinder charge air tube conveys compressed air past the air switch and to said pneumatic cylinder 11.

FIG. 2 shows the position of said air switch 21 and actuating trigger 22. Such air switches are commercially available and are old in the art.

FIG. 3 is a section taken through said adapter 13, tissue mount 14 and other elements showing that one end of said piston rod is threadably engaged into a hole 23 that extends coaxially through said adapter. Said tissue mount 14 is manufactured of a ferrous metal and is removably disposed in a recessed seat 24 of said adapter 13. Said tissue mount is held in position by means of one or more magnetic element 25 embedded within said adapter either at or in close proximity to said recessed seating surface. Said seating arrangement of said tissue mount facilitates quick changes of tissue mounts.

In this embodiment of the device a piston rod guide 26 is threadably attached onto the end of pneumatic cylinder 11. The adapter 13 and piston rod guide 26 can be easily unscrewed and are therefore interchangeable.

FIG. 4A shows said metal block 18 to which is affixed a backwardly projecting post 27 which is slidably mounted in a hole 28 through said upturned leg 17. Said backwardly projecting post 27 has cut into it a circumferential channel 29 which mates with a spring-loaded locking key or ball 30 seated at the top of intersecting hole 31. In this embodiment a small compressed spring 32 holds said key and ball in position. Compression of said spring can be varied by means of set screw 33. Said post and metal block is secured thereby in such a manner as to be easily removable.

Said metal rod 15 is held in position in said frame 10 by a means of a locking screw 34. Said metal rod can be removed from said frame and immersed in a flask or reservoir of cryogen or the assembled device can be hand-held with said upturned leg immersed in cryogen.

FIG. 4A also shows a metal cover 35, preferably brass, that fits over said upturned leg 17 and mirror metal block 18 during the immersion of the leg in cryogen. Said metal cover remains in place over said upturned leg after said metal rod is removed from said immersion flask to prevent condensation on the mirrored surface of said metal block and is removed just prior to performing a fixation of tissue material.

FIG. 5 shows the cutout 16 in said frame into which said metal rod 15 can be inserted and secured by means of said locking screw 34. In this embodiment a plate 36 is attached by screws or like fasteners onto the side of said handgrip. Plate 36 normally remains in place during use of the instrument and serves to hold locking screw 34 in position.

It should be noted that the various elements of this device can appear in different configurations without departing from the spirit or concept of the invention.

I claim:

1. A hand-held cryofixation apparatus comprising:
   a frame in the form of a piston handgrip into which is mounted a pneumatic cylinder and piston rod,
   an adapter and tissue mount attached to the end of said piston rod,
   an L-shaped metal rod slidably disposed in a slot or cutout in said frame, and
   a metal block with mirror finish attached to the upturned leg of said L-shaped metal rod.

2. The apparatus as recited in claim 1 wherein said adapter is threadably engaged onto the end of said piston rod.

3. The apparatus as recited in claim 2 wherein said tissue mount is removably disposed in a recessed seat in said adapter, said recessed seat being formed of magnetic elements.

4. The apparatus as recited in claim 2 wherein said tissue mount is removably disposed in a recessed seat of said adapter, said recessed seat having magnetic elements in close proximity thereto.

5. The apparatus as recited in claim 1 wherein said mirror finish of said metal block is disposed to face the line of travel of said piston rod, adapter and tissue mount.

6. The apparatus as recited in claim 1 wherein said pneumatic cylinder and piston rod can be activated by compressed air charges of predetermined pressure.

7. The apparatus as recited in claim 1 wherein a trigger actuated air switch is mounted within said piston handgrip.

* * * * *